United States Patent

Kohlert et al.

[11] Patent Number: 5,991,047
[45] Date of Patent: Nov. 23, 1999

[54] METHOD FOR CONTINUOUSLY CONTROLLING THE SHRINKAGE OF AN AMORPHOUS FILM, AND AN ARRANGEMENT HEREFOR

[75] Inventors: Christian Kohlert, Oberahr; Heinz Gaertner, Mettmann; Sven Behrendt, Montabaur; Lorenz Diener, Uffing, all of Germany

[73] Assignee: Klockner Pentaplast GmbH, Montabaur, Germany

[21] Appl. No.: 09/191,180

[22] Filed: Nov. 13, 1998

[30] Foreign Application Priority Data

Nov. 21, 1997 [DE] Germany .......................... 197 51 817

[51] Int. Cl.$^6$ ................................. G01N 21/84
[52] U.S. Cl. .................. 356/429; 250/548; 250/559.01; 250/559.02
[58] Field of Search .................................... 356/365, 367, 356/368, 32, 33, 429–431, 443, 444; 250/548, 559.01, 559.02, 559.09

[56] References Cited

U.S. PATENT DOCUMENTS

| | | | |
|---|---|---|---|
| 3,880,524 | 4/1975 | Dill et al. | 356/118 |
| 4,158,506 | 6/1979 | Collett | 356/365 |
| 4,547,664 | 10/1985 | Vogt et al. | 250/205 |
| 5,906,901 | 5/1999 | Tanimoto | 430/22 |

FOREIGN PATENT DOCUMENTS

| | | |
|---|---|---|
| 0 632 256 A1 | 1/1995 | European Pat. Off. . |
| 1951 920 | 4/1971 | Germany . |
| 24 30 521 | 1/1975 | Germany . |
| 32 12 809 A1 | 10/1983 | Germany . |
| 3931 540 A1 | 4/1991 | Germany . |
| 195 37 706 A1 | 4/1997 | Germany . |

Primary Examiner—Frank G. Font
Assistant Examiner—Layla Lauchman
Attorney, Agent, or Firm—Roberts & Mercanti,L.L.P.

[57] ABSTRACT

The shrinkage of a calendered amorphous film is continuously controlled during the taking off from a calender, the shrinkage being measured over the film width and the film length with the aid of the dichroism of the film. For this purpose, a shrinkage measuring instrument 51 supplies measured data concerning shrinkage of the film to a connected measured-data computer 52 which is connected, on the one hand, via an interface to a master computer 53, and, on the other hand, to a screen display 54. Characteristic calibration curve parameters of different film types and shrinkage deviations and/or of shrinkage limits are stored in the master computer and are, upon request, fed into the measured-data computer. The measured anisotropy of the film is converted into the respective shrinkage by means of a calibration curve, which is based on the calibration curve parameters. If the shrinkage is not within the prescribed limits, the master computer applies signals to the actuators for the purpose of controlling the friction and the rotational speed between the last calender roll and first take-off roll, for the purpose of temperature control or cooling the take-off and chill rolls, for the purpose of controlling the rotational speeds of the take-off rolls and for the purpose of the temperature control of the last calender roll.

28 Claims, 7 Drawing Sheets

$$\Delta S = t_{GM}/t_{GR} - 1 + b_{LKW}/b_{EAW} - 1 = t_{GM}/t_{GR} + b_{LKW}/b_{EAW} - 2$$

FIG. 10

METHOD FOR CONTINUOUSLY CONTROLLING THE SHRINKAGE OF AN AMORPHOUS FILM, AND AN ARRANGEMENT HEREFOR

BACKGROUND OF THE INVENTION

1. Field of the Invention

The invention relates to a method for continuously controlling the shrinkage of an amorphous film during taking-off from a calender, the shrinkage being measured over the film width and film length with the aid of the dichroism or the birefringence of the film, and an arrangement herefor.

2. Description of the Related Art

One of the conventional methods for processing plastics into films is calendering. In calendering, the material is traverses a nip only once and is brought in the process into a special geometric shape, whereas in rolling the material traverses a nip several times. For this purpose, a calenderable composition is firstly compounded and prepared with additives by mixing. The finished mixtures are plasticized, broken down, homogenized and applied to the calender in the form of a kneading mass. By contrast with the extrusion or injection molding of thermoplastics, in this case the process steps of gelling, homogenizing and shaping take place not inside one machine but one after another in separate units. Rolling out the kneading mass to form a sheet gives the material a preliminary shape with reference to thickness and width. The film is then removed or taken off from the calender, the film being guided over take-off rolls, after which the hot film is cooled, running over chill rolls, and finally relatively long film webs are wound up, or short film pieces are cut into lengths and stacked. During cooling, the film traverses the thermoplastic region, in which tensile stresses lead to orientations and frozen-in stresses inside the film. Films which have been wound up or cut into lengths are further processed by the customer using thermal methods and must have specific shrinkage properties depending on the thermoforming plant used for this purpose and on the thermoforming method applied. Shrinkage therefore constitutes a quality property of amorphous films, it being necessary for the maintenance of the shrinkage to be detected by measurement and to be adhered to by changing process parameters when taking off the film from the calender.

Film shrinkage is based on a molecular orientation which is to be ascribed in the case of calendering to the deformation of the melt in the course of the process and to the shearing of the thermoplastic. Deformations will be produced, inter alia, as follows:

by the plasticizing of the raw material in the kneader,
from the technology of wide flow and from the shearing and elongation of the melt in the nips,
by stretching of the film upon deflection around the take-off rolls,
by stretching of the film in the region of the air gaps between the chill rolls.

The intensity of the orientation depends on the degree of the deformation, on the temperature profile, on the cooling time and/or the cooling profile, and on various material parameters. As a reaction to the introduction of orientations during production, the films shrink when they have to be heated, for example, upon thermoforming or some other later processing. Thus, for example, rigid PVC films, which generally do not contain plasticizers, but only additives as processing aids, are processed to form thermoformed beakers, containers, dishes, blister packs, sorting bases for fruit, chocolates, confectionery or small industrial parts. Further applications of rigid PVC films are to be found in the building of apparatus and in the automobile industry, in the building sector and in special fields such as, for example, the production of identity cards, such as credit cards, pass cards, key cards, phone cards etc.

Generally speaking, shrinkage denotes the dimensional change, in particular the change in length and width of a film as a consequence of the effect of heat. In the case of conventional shrinkage measurement, the films are stored at the prescribed temperature in a circulating air drying cabinet or in a liquid bath; the shrinkage occurring after a specific time is measured at room temperature. In the DIN Standard 53377, the determination of the shrinkage of a film is laid down in such a way that a square test piece with an edge length of 100 mm is conditioned in an oven for 10 minutes at 140° C. The sample is subsequently measured after having cooled. The difference between the initial dimension before the heat treatment and the final dimension after the heat treatment is determined by length measurement, and the measured value is specified as shrinkage S in %. It then holds for this shrinkage S that $$s = \frac{dl}{l_0} = \frac{l_0 - l_1}{l_0}$$

Other storage times and temperatures in the measurement of the film shrinkage are conditioning over 15 minutes at a temperature of 100° C. and heat treatment over 5 minutes in water at a temperature of between 70 and 95° C. A number of errors can occur in this conventional shrinkage measurement according to DIN, such as:

fluctuations in the dimensions of the samples owing to the punch which is used to produce the square test piece,
twisting of the punch with respect to the longitudinal direction of the film,
temperature fluctuations in the heating oven,
fluctuations in the conditioning time in the heating oven,
inaccuracies in the determination of the geometric dimensions.

The said errors lead to a fluctuation of up to 36% in the shrinkage value determined. This substantial inaccuracy brings conventional shrinkage measurement into question, in particular even slight deviations from the stipulated temperature in the heating oven in the interval from 120° C. to 160° C. lead to significant shrinkage deviations. A further disadvantage of conventional shrinkage measurement consists in that it is impossible to take account of the mutual influence of longitudinal, transverse and thickness shrinkage. The traditional description of shrinkage proceeds from a one-dimensional consideration of the change in length. Since, however, films are three-dimensional structures, the change in a dimension must depend on the two other dimensions if the latter are not negligibly small. In the case of a film thickness in the range from 60 $\mu$m to 1000 $\mu$m, it is certainly permissible to neglect the thickness shrinkage in contrast with the longitudinal and transverse shrinkage. In order to be able to make an unambiguous statement with respect to longitudinal and transverse shrinkage, it is appropriate for the test piece to be punched out in the machine direction of the film in order to measure the longitudinal shrinkage, and for it to be punched out transverse to the machine direction in the case of measuring the transverse shrinkage. In the first case, the width of the test piece is to be small by contrast with the length, while in the second case the length is, conversely, to be small by contrast with the width.

As already indicated above, the cause of the shrinkage resides in the elongation of the film above the glass transition temperature. The elongation orients the molecule chains, which are then frozen by the subsequent cooling to below the glass transition temperature. Upon later reheating above the glass transition temperature, the frozen-in stresses are released again and the molecule chains reassume their original configuration. Restoring forces (shrinkage forces) which cancel the initial deformation are produced as a consequence of the entropy change occurring in such cases. It is known that the orientation of the molecule chains in an amorphous film causes changes in the birefringence and the dichroism of the films, with the result that it is possible by measuring the dichroism or the birefringence to determine the orientation of the molecule chains, thus also to determine the shrinkage properties.

The shrinkage is influenced by
the control of the temperature and speed of the film web when being taken off downstream of the calender,
additives which influence the glass transition temperature of the film,
additives which influence the stretching behavior of the film, and
design measures aimed at reducing relaxation.

According to the invention, the shrinkage is measured by making use of optical properties of a polymer which are based on anisotropy effects, specifically dichroism and birefringence. Dichroism, also denoted as directionally dependent absorption of polarized light, embodies the second moment of the orientation distribution of molecule chains in a polymer. In this case, the intensity of the absorbed light depends on the vector direction of the incident beam relative to the orientation direction, the polarized light being absorbed to different degrees perpendicular and parallel to the stretching direction.

Birefringence describes the difference between the refractive indices of two mutually perpendicular principal axes, and likewise the second moment of the orientation distribution. Because of the optical anisotropy, that is to say different refractive indices, the light beam incident on a sample is split into two polarized, mutually perpendicular component beams with varying rates of propagation. After the sample has been left, there is a phase difference between the component beams which, when multiplied by the wavelength of the incident light yields the path difference $$\Gamma = \frac{\lambda \cdot \varphi}{2\pi} = d(n_{parallel} - n_{perpendicular})$$

wherein Γ=path difference.
λ=wavelength of the incident light beam.
φ/2Π=phase difference between the component beams in which the incident light beam is split.
d=thickness of sample.
$n_{parallel}$=index of refraction of the component beam parallel to the propagation direction of the incident light beam.
$n_{perpendicular}$=index of refraction of the component beam perpendicular to the propagation direction of the incident light beam.

The birefringence itself is yielded from $$\Gamma/d = n_{parallel} - n_{perpendicular}$$

The orientation of the molecules corresponds to the shrinkage capacity of the polymer or of the film. The transmission behavior of light transilluminating the film changes with the degree of orientation. In the case of rotation of a film which is located between a polarizer and an analyzer, the transmission of the light depends on the twisting angle of the film. In this case, the directions of polarization of the polarization filters, that is to say of the polarizer and analyzer, are perpendicular to one another. In order to improve the intensity of the light transilluminating the film in a specific mutual positioning of the polarizer and analyzer, the orientation of molecule chains in the film can be determined as follows. The film is held in the machine direction parallel to the passing direction of the polarizer or analyzer and subsequently rotated until a maximum value arises at the detector. The angle of rotation of the film is then equal to η, and the angle ε which the molecule chains form with the machine direction is then yielded as $$\epsilon = 45° - \eta$$

If the molecules are orientated in the machine direction, ε=0, since then the first maximum of the change in intensity is η=45°.

DE-C-24 30 521 describes a method and a device by means of which the state of polarization of a beam, that is to say its ellipticity and direction of polarization, can be determined by means of a rotating analyzer, the intensity of the beam passed being plotted as a function of the angle of rotation of the analyzer. Fourier analysis permits the ellipticity parameters to be determined. Also known are arrangements without moving elements which operate with a plurality of fixed detectors. In this case, the main beam to be analyzed is split into a plurality of component beams, or a plurality of detectors are arranged inside a main beam. In DE-A-32 12 809, a grating is used to split the main beam of a laser pulse into two component beams by diffraction into higher orders. This permits the simultaneous measurement of two mutually perpendicular directions of polarization, but this measurement does not suffice to provide a general characterization of the state of polarization of the laser pulse. DE-A-19 51 920 describes an arrangement having four fixed detectors and a cone which is used for beam splitting. However, the adjustment of the four independent beams is very complicated and susceptible to interference.

The position is similar for the analyzer device described in DE-A-39 31 540, in which splitting into six component beams is performed. Four component beams are used to characterize the ellipticity. The beam-splitting polarimeter used here is limited to splitting into a few component beams, in order to keep the technical outlay within bounds. The accuracy of rotating analyzers cannot be achieved with such polarimeters. U.S. Pat. No. 4,158,506 and EP-A-0 632 256 describe arrangements in which a plurality of detectors are placed inside the main beam. The power density, and thus the measuring sensitivity decreases strongly in a corresponding way owing to the expansion.

DE-A-19 537 706 discloses for the purpose of online monitoring of the birefringence of foils, films and sheets a rotation-free arrangement and an analyzing method in which the main beam to be analyzed is split with the aid of a two-dimensional diffracting structure into a number of component beams of the same beam profile and the same intensity, the component beams traversing elements sensitive to linear polarization and impinging on the corresponding number of detectors whose signals are subjected to Fourier analysis with respect to directions.

It is the object of the invention to create a method for continuously controlling the shrinkage of a film during taking-off from a calender, in which the shrinkage is continuously measured and account is taken of the mutual influence and/or correlation of longitudinal and transverse shrinkage and, moreover, the shrinkage is controlled within prescribed shrinkage limits. Within the scope of this object, the aim is also to measure the shrinkage of the films continuously with the aid of the dichroism and/or the birefringence over the width of the film web.

SUMMARY OF THE INVENTION

The invention provides a method for continuously controlling the shrinkage of an amorphous film during removal from a calender having a plurality of sequential calender rolls followed by a plurality of sequential takeoff rolls and then optionally a plurality of chill rolls, comprising continuously measuring film shrinkage values in the middle and at an edge of the film over the film width and film length by measuring the dichroism or the birefringence of the film, calculating an average shrinkage for the middle and an edge of the film to form a shrinkage difference $\Delta S$ from a plurality of continuously measured shrinkage values, and wherein in the event of a deviation of greater than ±0.5% of the shrinkage difference from a prescribed shrinkage difference, altering at least one of the friction, temperature, or rotational speed parameters of at least one calender roll, take-off roll, or chill roll such that the shrinkage difference $\Delta S$ is kept within the range of the prescribed shrinkage difference ±0.5% deviation.

The invention also provides an arrangement for continuously controlling the shrinkage of an amorphous film during removal from a calender having a plurality of sequential calender rolls followed by a plurality of sequential take off rolls and then optionally a plurality of chill rolls, comprising a shrinkage measuring instrument which supplies measured data concerning the shrinkage of the film to a connected measured-data computer which is connected via an interface to a master computer and to a screen display, wherein characteristic calibration curve parameters of different film types and shrinkage deviations and/or shrinkage limits are stored in the master computer and are fed into the measured-data computer which uses a calculated shrinkage difference and a measured shrinkage difference between the film middle and a film edge to determine a deviation in the shrinkage difference $\Delta S$ and to relay it to the master computer, and wherein the master computer is connected to actuators capable of altering the friction, temperature, and the rotational speed of the calender rolls, the take-off rolls, and chill rolls, and means for independently applying control to the actuators.

This object is achieved according to the method in such a way that the shrinkage is measured continuously in the middle and at the edge of the film, that use is made of an average shrinkage for the middle and the edge to form a shrinkage difference $\Delta S$ from a number of measured shrinkage values, and that in the event of a deviation of greater than ±0.5% of the shrinkage difference from a prescribed shrinkage difference, at least one of the parameters such as the friction and the rotational speed between the last calender roll and the first take-off roll, the temperature and the rotational speed of the calender and take-off rolls is altered such that the shrinkage difference $\Delta S$ is kept within the range of the prescribed shrinkage difference ±0.5% deviation.

In a development of the method according to the invention, the time up to reaching the glass transition temperature in the middle and at the edge of the film taken off from the calender, as well as the film widths on the last calender roll and the first take-off roll are measured, and a shrinkage difference $\Delta S$ between the middle and the edge is determined in accordance with the approximate formula $$\Delta s = \frac{t_{GM} - t_{GR}}{t_{GR}} + \frac{b_{LEW} - b_{EAW}}{b_{EAW}}$$
$$= t_{GM} / t_{GR} + b_{LEW} / b_{EAW} - 2$$

using the times $t_{GM}$, $t_{GM}$ for reaching the glass transition temperature in the middle of the film and at the edge of the film and the film widths $b_{LKW}$, $b_{EAW}$ on the last calender roll and the first take-off roll, and this shrinkage difference $\Delta S$ is minimized.

In one embodiment of the method, the temperature of the film surface is measured in the middle and at the edge on the take-off rolls by means of an infrared camera. Moreover, the film width on the last calender roll and the first take-off roll is measured with the aid of a CCD device.

In one embodiment of the method, for the purpose of shrinkage measurement, the film is transilluminated with linearly polarized laser light in the wavelength region from 400 to 900 nm, in particular 670 nm, and the orientation of the plane of polarization of the laser light is inclined with respect to the film longitudinal direction, as a result of which upon transilluminating the film the linearly polarized laser light is partially circularly polarized and reformed by means of an optical system in a linearly polarized main beam which a downstream diffracting element splits into n component beams of which each is directed onto a photoelement, equipped with a polarization filter, of a detector ring.

The invention is also intended to achieve the object of creating an arrangement for continuously controlling the shrinkage of an amorphous film during taking-off from a calender, which permits quick detection and control of the shrinkage via the dichroism and/or the birefringence of the film, and operates in a way which largely facilitates adjustment and is not vulnerable to interference.

In order to achieve this object, an arrangement is provided which is defined in that a shrinkage measuring instrument supplies measured data concerning the shrinkage of the film to a connected measured-data computer which is connected, on the one hand, via an interface to a master computer and, on the other hand, to a screen display, in that characteristic calibration curve parameters of different film types and shrinkage deviations and/or shrinkage limits are stored in the master computer and are, upon request, fed into the measured-data computer which uses the calculated shrinkage difference and the measured shrinkage difference between the foil middle and the foil edge to determine the deviation in the shrinkage difference $\Delta S$ and to relay it to the master computer, and in that the master computer is connected to actuators for the friction and the rotational speed between the last calender roll and first take-off roll, for the temperature control or cooling of the take-off and chill rolls, for the rotational speed of the take-off rolls and for the temperature control of the last calender roll, and control signals are applied to individual, to pairs of, to a plurality of, or simultaneously to all the actuators.

The invention provides the advantages of quickly detecting the orientation of the molecule chains in films, as a result of which it is possible for the shrinkage to be measured and controlled quickly, and such measurement and controlling result in substantial savings in time and material, since control is already being exercised during the process of producing the films, and the scrapping of film material can therefore be kept at a very low level.

BRIEF DESCRIPTION OF THE DRAWINGS

The invention is explained in more detail below with the aid of the drawings, in which.

DETAILED DESCRIPTION OF THE PREFERRED EMBODIMENT

Figure 1:
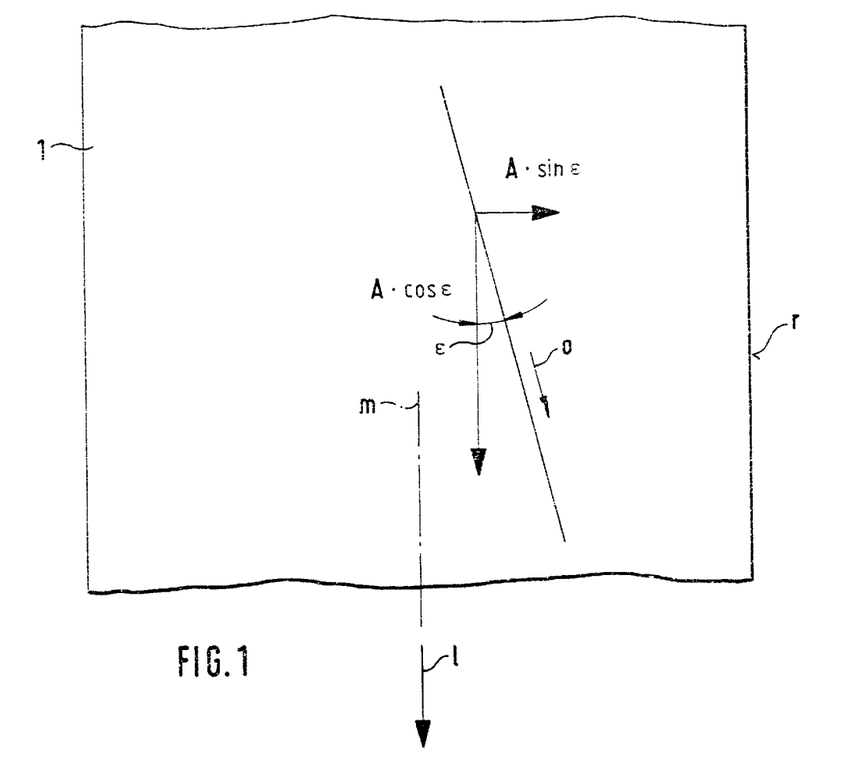
FIG. 1 shows a correlation of the measured value amplitude, which reproduces a measure of the molecule chain orientation in a calendered film, relating to the longitudinal and transverse shrinkage of the film.

The correlation of a measured value amplitude relating to the longitudinal and transverse shrinkage of a calendered film 1 is described with the aid of FIG. 1. The amplitude A is a vector which shows the degree of orientation of the molecules or molecule chains, which are orientated in the direction o. The direction of orientation o of the molecule chains encloses an angle $\epsilon$ with the running direction l of the film and/or with the machine direction. The longitudinal shrinkage is thus produced in accordance with the expression $A \cdot \cos \epsilon$, and the transverse shrinkage is described by the expression $A \cdot \sin \epsilon$. The longitudinal and transverse shrinkages are thus correlated with one another by the angle $\epsilon$. The letter r denotes the film edge, and m the film middle. If a shrinkage measuring instrument traverses the film width for the purpose of determining the film shrinkage, the film simultaneously moving in the direction l, both the longitudinal and the transverse shrinkages are measured. During the measurement of the shrinkage, it is seen that there is generally a shrinkage difference between the film middle m and the film edge r in the range of 0.5% to 2.5%, this shrinkage difference being calender-specific, that is to say being a function of whether the first take-off rolls run "cold" at a temperature of 35 to 55° C., or the first take-off rolls are heated up to 80 to 85° C., being produced, so to say, with "hot" take-off rolls. It emerges in this case that the shrinkage profile over the film width is influenced by the temperatures of the first take-off rolls, and that the shrinkage difference is less for so-called "hot" take-off rolls than for "cold" take-off rolls.

The temperature profile over the film width, as measured on the take-off rolls, exhibits a similar shape to the shrinkage profile over the film width. In this case, a lower film edge temperature by comparison with the temperature in the film middle leads to a larger amount of longitudinal shrinkage, and a higher temperature in the film middle leads to a lesser amount of shrinkage. Investigations by means of targeted conditioning of specific regions over the film width have shown that the shrinkage value can be influenced in these regions. Thus, the longitudinal shrinkage of the film can be controlled by a change in the shrinkage by blowing air onto the film web while it is being taken off, doing so in the film middle, in a region between the film middle and the film edge and at the film edge using cold or warm air. It emerges in this case that blowing air onto the film web on the take-off rolls at specific points leads to an increase in the amount of longitudinal shrinkage in the case of cold air. The use of warm air at the film edge can reduce the shrinkage to the measure of the shrinkage in the film middle by virtue of a lengthened relaxation time. It may be stated in summary that the temperature profile of the film over the width has a substantial influence on the shrinkage profile. In this cases colder regions lead to a higher amount of longitudinal shrinkage, and warm regions to a lesser amount of longitudinal shrinkage. In order to achieve as uniform as possible a shrinkage profile over the film width, that is to say in order to minimize the shrinkage differences between the film edge and film middle, it is necessary to ensure a temperature which is as uniform as possible over the film width. This uniform temperature profile over the film width can be implemented, on the one hand, by blowing cold air onto the warmer film middle or, alternatively, by blowing hot air onto the colder film edges.

Figure 2:
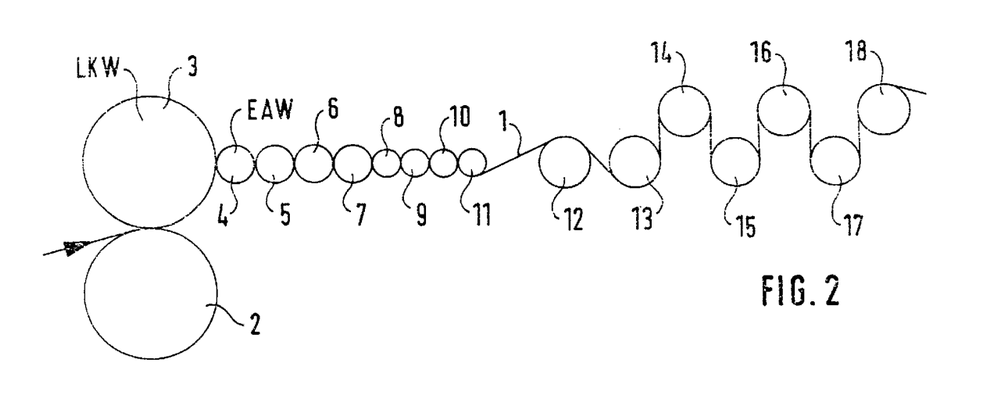
FIG. 2 shows a diagram of the take-off and chill rolls, which are connected downstream of a calender.

Represented diagrammatically in FIG. 2 is the take-off of a calender (not shown), which comprises a first group of take-off rolls 4 to 7, a second group of take-off rolls 8 to 11 and a group of chill rolls 12 to 18. The first group of the take-off rolls 4 to 7 has, for example, a larger diameter than the second group of take-off rolls 8 to 11. The first take-off roll (EAW) 4 makes contact with the last calender roll (LKW) 3 which, in turn, makes contact with a further calender roll 2. These calender rolls can, for example, be the two last calender rolls of a four-roll L calender. The course of the film 1 between the two calender rolls 2 and 3, the take-off rolls 4 to 11 and the chill rolls 12 to 18 is represented diagrammatically in FIG. 2. In practice, the temperature profiles on the take-off rolls are measured with the aid of an infrared camera. Since, for technical reasons, it was possible to measure respectively only the take-off rolls 5, 7, 9 and 11, which had temperature differences of 7° C., 5° C., 4° C. and 3° C. between the roll middle and the roll edge, the same temperature difference was respectively assumed for the take-off rolls 4, 6, 8 and 10 mounted upstream thereof as for the take-off roll respectively downstream. Using the measured temperature profiles of the individual take-off rolls, the respective temperature characteristic can be determined as a function of time in the middle of the take-off roll, and it is therefore possible to measure the variation in cooling curves. Moreover, the cooling curves can theoretically be calculated using a model which will not be considered in more detail here. In this case, the theoretically calculated cooling curves exhibit good agreement with the measured cooling curves, with the result that the model can be applied for simulation calculations aimed at preliminary calculation of the effects of temperature fluctuations over the film width, as well as at determining the influence of different roll speeds on the smoothing out of the film properties. It emerges with these calculations that the temperature characteristic is such that in the case of a PVC film the transition to below the glass transition temperature of approximately 80° C. is realized later in the film middle than at the film edge with reference to the exit of the film from the last calender nip. In intimate association therewith, there is then a shrinkage difference in the longitudinal shrinkage in the film middle and at the film edge. This shrinkage difference can be described mathematically by the following approximate formula:

$$\Delta s = \frac{t_{GM} - t_{GR}}{t_{GR}} + \frac{b_{LEW} - b_{EAW}}{b_{EAW}}$$

using the times $t_{GM}$, $t_{GR}$ for reaching the glass transition temperature in the film middle and at the film edge and the film widths $b_{LKW}$, $b_{EAW}$ on the last calender roll 3 and $$=t_{GM}/t_{GR}+b_{LKW}/b_{EAW}-2$$

of the first take-off roll 4.

With the aid of this approximate formula, it is possible by appropriately controlling different parameters in the take-off of the calender to minimize the shrinkage difference $\Delta S$ and to automate the calendering process, as will further be explained later with the aid of FIGS. 9 and 10.

Figure 3:
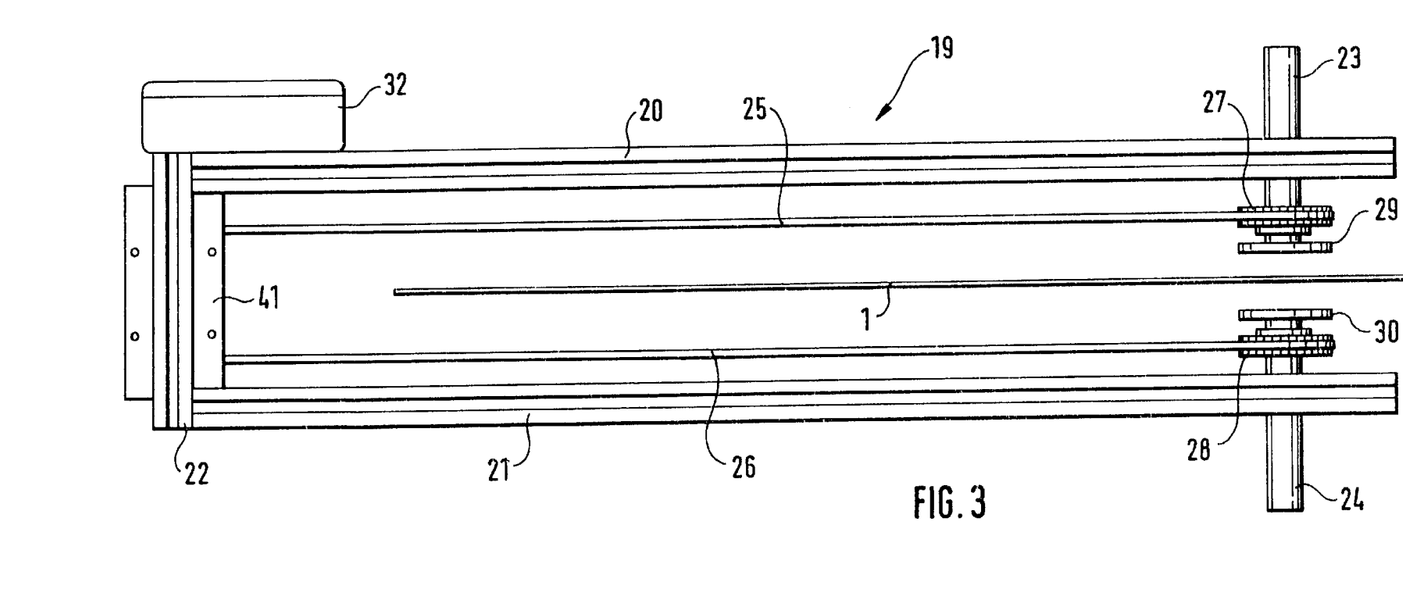
FIG. 3 shows a diagrammatic view of a first embodiment of a shrinkage measuring instrument with a rotatable measuring head.

A first embodiment 19 of a shrinkage measuring instrument is described with the aid of FIG. 3. The shrinkage measuring instrument has a frame made from a U-profile 20, 21, 22, which is a metal profile, in particular made from aluminum. A measuring head comprises a light source 73, which is a laser, and a receiver 74 (see FIG. 4). The measuring head can be displaced in its entirety along the limbs 20, 21 of the U-profile, the lengths of the limbs being selected such that the measuring head can be displaced as far as into the web middle of the film 1, which runs through between the two limbs as well as between the light source 73 and the receiver 74. The displacement of the measuring head as far as into the middle of the film 1 suffices, since the shrinkage characteristic is symmetrical with reference to the calender axis and/or to the machine direction and/or film running direction. The light source 73 and the receiver 74 are each individually installed in a cylindrical tube 23 and 24, respectively, which are aligned perpendicular to the limbs 20 and 21 of the U-profile. The two cylindrical tubes 23, 24 are mounted opposite one another and adjusted about the optical axis between the light source and receiver. Each cylindrical tube 23, 24 is connected on the outside to a toothed disk 27 and 28, respectively, over which there is guided an endless flat toothed belt 25 or 26 which, at the other end of the U-profile, runs around a further toothed disk 35 or 36, which is seated on a shaft 34 which is driven by a motor 32 which is fastened on the outside of the limb 20. A rotary part 29 or 30 is mounted on the end face of each cylindrical tube 23 or 24 pointing towards the film 1.

Figure 4:
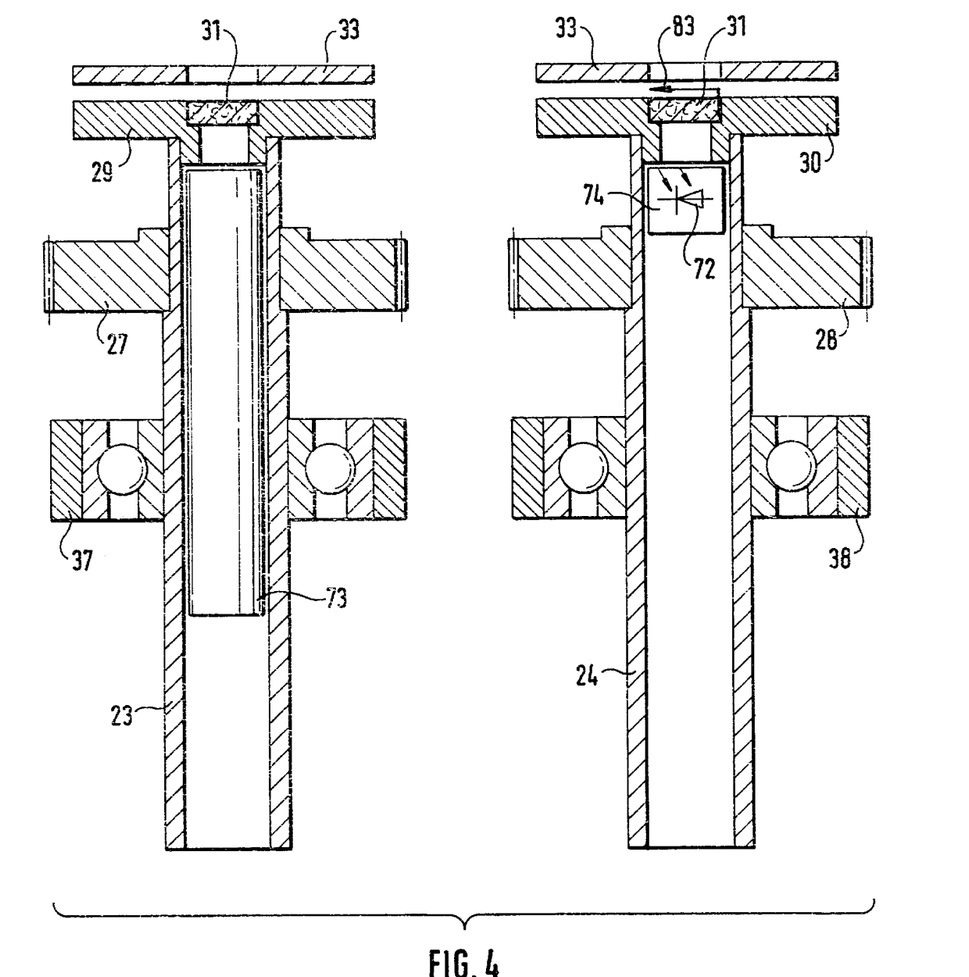
FIG. 4 shows a section through a cylindrical tube for holding a light source or a receiver of the shrinkage measuring instrument according to FIG. 3.

FIG. 4 shows one section each through cylindrical tubes 23 and 24, it being necessary to note in this connection that the cylindrical tubes are of identical construction. To this extent, all the statements on the cylindrical tube 23 also apply analogously to the cylindrical tube 24. The cylindrical tube 23 is mounted in a pedestal bearing housing 37, and supports the toothed disk 27 on its outside. The cylindrical tube 23 largely encloses the light source 73, which is a laser which radiates light in the wavelength region from approximately 400 to 900 nm, in particular in the red wavelength region of 670 nm. Located in the rotary part 29, which is pushed into the cylindrical tube 23, is a polarization filter 31 which acts as a polarizer for the monochromatically polarized light of the laser. The direction of polarization of the polarization filter 31 can be altered as desired by rotating the rotary part 29. A cover plate 33 seals the rotary part 29. Located instead of the light source in the cylindrical tube 24 is the receiver 74, which comprises a photoelement 72, for example a silicon photoelement, which supplies a current of specific amplitude as a function of the light intensity occurring. This current is converted by an impedance transformer (not shown) into a voltage, amplified by a measuring amplifier and read into a computer via a serial interface. In the cylindrical tube 24, the polarization filter 31 forms the analyzer for the light transilluminating the film. The photoelement 72 has a sensitivity range of 400 nm to 1100 nm, for example, and is located in a plastic housing which is positioned in the cylindrical tube 24. The polarization filter 31 and/or the analyzer, which is arranged above the receiver 74, is likewise located in a housing, to which there is additionally attached an angular scale 83 which can be used to determine the respective angle of rotation of the analyzer with respect to the main beam of the laser, and thus to determine the light intensity as a function of the angle of rotation at the receiver 74.

Figure 5:
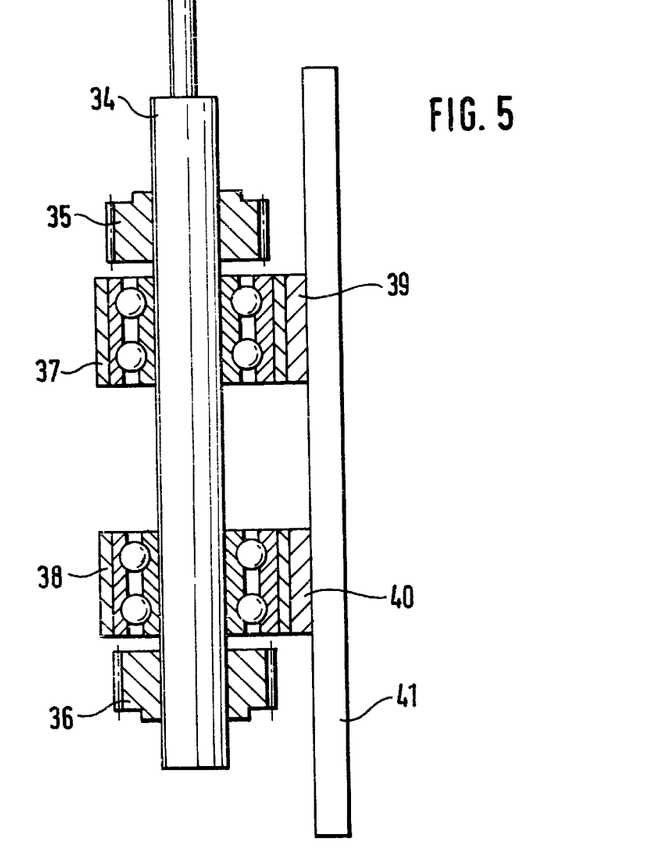
FIG. 5 shows a detail of a drive shaft for the shrinkage measuring instrument according to FIG. 3.

FIG. 5 shows a plan view of the shaft 34 on which there are seated two toothed disks 35 and 36 which have a smaller diameter of the toothed disk than do the toothed disks 27, 28 on the cylindrical tubes 23, 24. The shaft 34, which is driven by the motor 32 (see FIG. 3), is mounted in pedestal bearing housings 37, 38. These pedestal bearing housings 37, 38 are fastened via distance pieces 39, 40 to a base plate 41 which is connected to the metal profile 22 (see FIG. 3). The motor-driven shaft 34 sets rotating the endless flat toothed belts 25, 26 and, in a synchronous fashion, the cylindrical tubes 23, 24 and, thus, the light source 73 and the receiver 74. The sense of rotation of the motor 32, which is an electric motor, is reversible, which is required because the power cables permit only a limited number of rotations in one direction. The measuring head comprising the light source 73 and the receiver 74 can be displaced in its entirety along the limbs 20, 21 of the U-profile (shown in FIG. 3) as far as into the web middle of the film 1, which runs through between the two limbs as well as between the light source 73 and the receiver 74 (perpendicular to the plane of the drawing sheet of FIG. 3). Two linear guides (not shown) attached to the calender line are provided for the traversing, that is to say the transverse movement relative to the machine direction of the measuring heads respectively of the shrinkage measurement instrument.

Figure 6:
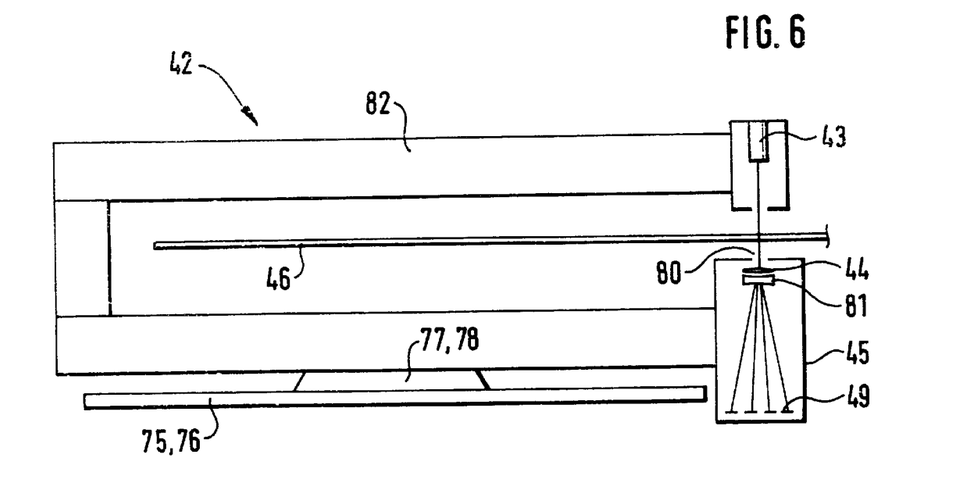
FIG. 6 shows a diagrammatic view of a second embodiment of a shrinkage measuring instrument.

FIG. 6 shows a diagram of a second embodiment 42 of the shrinkage measuring instrument, which comprises a laser as light source 43 and a receiver 45 which comprises an optical system 44, a diffracting element 81 and a detector ring 49. The design of this second embodiment of the shrinkage measuring instrument is similar to the design of the first embodiment, and has a frame made from a U-profile 82, the laser 43 being fastened on one limb, and the receiver 45 being fastened on the other limb of the U-profile 82. A film 46 runs through the U-profile 82 perpendicular to the plane of the drawing and is transilluminated by the beam of the laser 43. The laser 43, which has a power of approximately 3 mW, radiates polarized light in the red wavelength region. The orientation of the plane of polarization of the laser light is, for example, inclined by 45° with respect to the machine direction. Upon transilluminating the film 46, this linearly polarized light is circularly polarized to a certain extent. The circularity is caused by the different birefringence-induced transmission phases of the energy vectors, which are all directed in the orthogonal orientation direction of the film 46. The degree of circularity depends on the orientation of the molecule chains. The energy vectors describe an ellipse whose semimajor axis is likewise inclined by 45° with respect to the machine direction. The transmitted circular light is reformed into linearly polarized light by means of the optical system 44. Two mutually parallel linear guides 75, 76 arranged one behind another in the block direction are indicated diagrammatically in FIG. 6. The linear guides are attached near the calender line transverse to the running direction of the film 1. The linear guides are fitted with two guide carriages 77, 78 on which the respective embodiment 42 or 19 of the shrinkage measuring instrument is fastened. The guide carriages 77, 78 are driven by motor.

Figure 7:
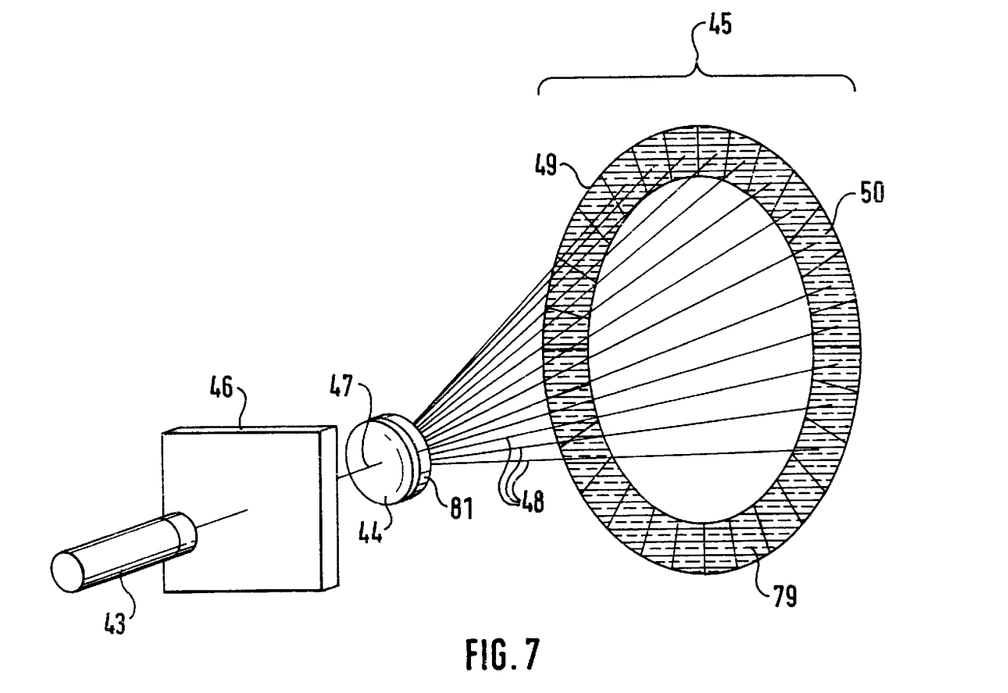
FIG. 7 shows a diagram of an optical system and a receiver of the second embodiment of the shrinkage measuring instrument according to FIG. 6.

Represented diagrammatically in FIG. 7 is the measuring head comprising a laser 43, an optical system 44, a diffracting element 81 and the detector ring 49 of the receiver 45. The detector ring 49 comprises a number n of photoelements 50. The diffracting element 81 downstream of the optical system 44 splits the main beam 47 of the light which is passed through the film 46 into n component beams which in each case impinge on a photoelement 50. A polarization filter 79 is arranged on each photoelement 50. The number n of the photoelements 50 lies in the range of 18 to 72 and, in particular is n=36. The direction of polarization of a polarization filter 79 relative to the neighboring polarization filter 79 is rotated in each case by an angle of the order of magnitude of 360°/n in the radial direction of the detector ring 49 about the optical axis of the main beam 47 of the light source 43. If, for example, n=36, the direction of polarization of the polarization filter 79 is rotated by 10° in each case. This design therefore permits the transmitted light to be measured over the entire angle of 360° without the need to provide a rotating analyzer as polarization filter. To this extent, the entire measuring arrangement of the shrinkage measuring instrument in accordance with the second embodiment 42 operates without a rotating analyzer, it being the case, however, that the beam intensity of the individual component beams is of the same magnitude with the result that no difference in intensity occurs between the component beams. As may be seen from FIG. 6, the optical system 44 is located between an inlet opening 80 into the receiver housing and the detector ring 49.

Figure 8:
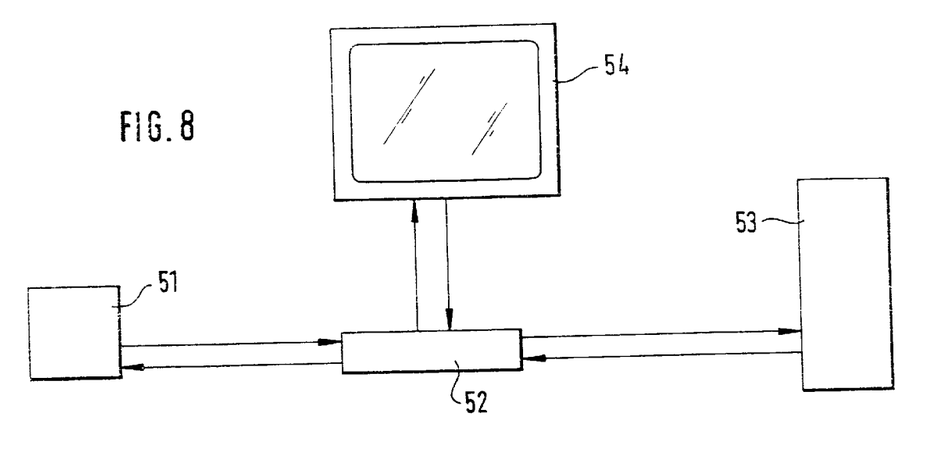
FIG. 8 shows a block diagram of the connection of a shrinkage measuring instrument to a measured data computer and a master computer.

FIG. 8 shows a block diagram of the connection of the shrinkage measuring instrument 51 to a measured-data computer 52 and a master computer 53. The shrinkage measuring instrument 51, which is present either in the first embodiment 19 or in the second embodiment 42, supplies measured data concerning the shrinkage of the film to the connected measured-data computer 52 which is connected, on the one hand, via an interface to the master computer 53 and, on the other hand, to a screen display 54. Characteristic calibration curve parameters a, b, c, d as explained in the following description of a calibration curve f(y) of different film types and shrinkage deviations and/or shrinkage limits for the individual film types are stored in the master computer 53. The stored characteristic calibration curve parameters and the shrinkage deviations and/or shrinkage limits of the individual film types are fed into the measured-data computer 52 by the master computer 53 on the basis of the interrogation of the measured-data computer 52. The deviation of the shrinkage difference ΔS from the calculated and the measured shrinkage difference is determined in the measured-data computer, and this deviation is relayed to the master computer 53. The master computer 53 is connected to actuators 62 to 68 (compare FIG. 10) for the friction and the rotational speed between the last calender roll 3 and first take-off roll 4, for the temperature control or cooling of the take-off and chill rolls 4 to 11 and 12 to 18, respectively, for the rotational speed of the take-off rolls 4 to 11 and for the temperature control of the last calender roll 3. The master computer 53 applies control signals to the actuators 62 to 68 either to individual, to pairs of, to a plurality of, or simultaneously to all the actuators, in order, depending on what is required, to control the parameters in the take-off of the calender in the desired way.

Evaluating the anisotropy value measured by the respective receiver of the shrinkage measuring instrument 51 requires conversion of the anisotropy values into shrinkage values, use being made for this purpose of a calibration curve which contains the previously mentioned characteristic calibration curve parameters a, b, c, d in a polynomial of 3rd degree in accordance with the formula $$f(y) = a + bx + cx^2 + dx^3$$

where f(y) is the anisotropy and x the shrinkage. The calibration curve parameters a to d, which are characteristic of the respective film type, are selected such that an empty measurement, that is to say a measurement without a film in the beam path of the shrinkage measuring instrument is carried out. In this case, the calibration curve parameters are fixed such that the "shrinkage values" of the empty measurement correspond to the anisotropy values.

The anisotropy values and the shrinkage values are output simultaneously and in graphic form on the screen display 54. By way of example, 100 values are always output on the screen display during a measurement, each value being composed, in turn, from an arbitrary number of averagings. An averaging of 50 signifies that 50 measured values are taken internally and used to form the arithmetic mean, which is then displayed. In addition, the 100 shrinkage values taken during a series of measurements are averaged in turn and displayed, together with the standard deviation, as digital values.

The calibration curves are checked by measuring on the corresponding film type.

Figure 9:
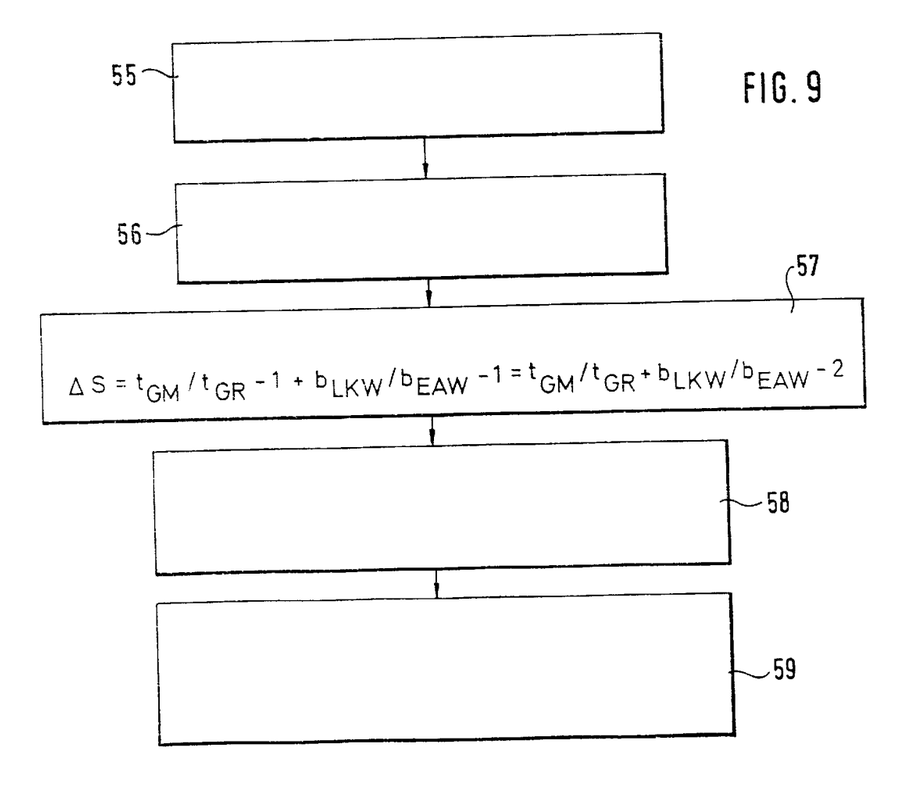
FIG. 9 shows a diagram of a control loop for minimizing the shrinkage difference.

The automatic control or regulation in the take-off of the calender for the purpose of minimizing the shrinkage difference ΔS over the film width is performed in the control loop represented diagrammatically in FIG. 9.

This control loop comprises means 55 for temperature measurement, means 56 for film width measurement, means 57 for calculating the theoretical shrinkage difference ΔS, means 58 for controlling the film temperature and means 59 for controlling the constriction effect between the last calender roll and the first take-off roll. The means 55 is, for example, an infrared camera or an IR scanner for measuring the film surface temperature on the take-off rolls 4 to 11, the surface temperatures being measured both at the film edge and in the film middle (compare FIG. 2). The means 56 is, for example, a charge coupled device, i.e. a CCD device by means of which the film width on the last calender roll 3 and the first take-off roll 4 is measured. The calculation of the theoretical shrinkage difference is performed in the means 57 in accordance with the equation $$\Delta s = \frac{t_{GM} - t_{GR}}{t_{GR}} + \frac{b_{LEW} - b_{EAW}}{b_{EAW}}$$

Figure 10:
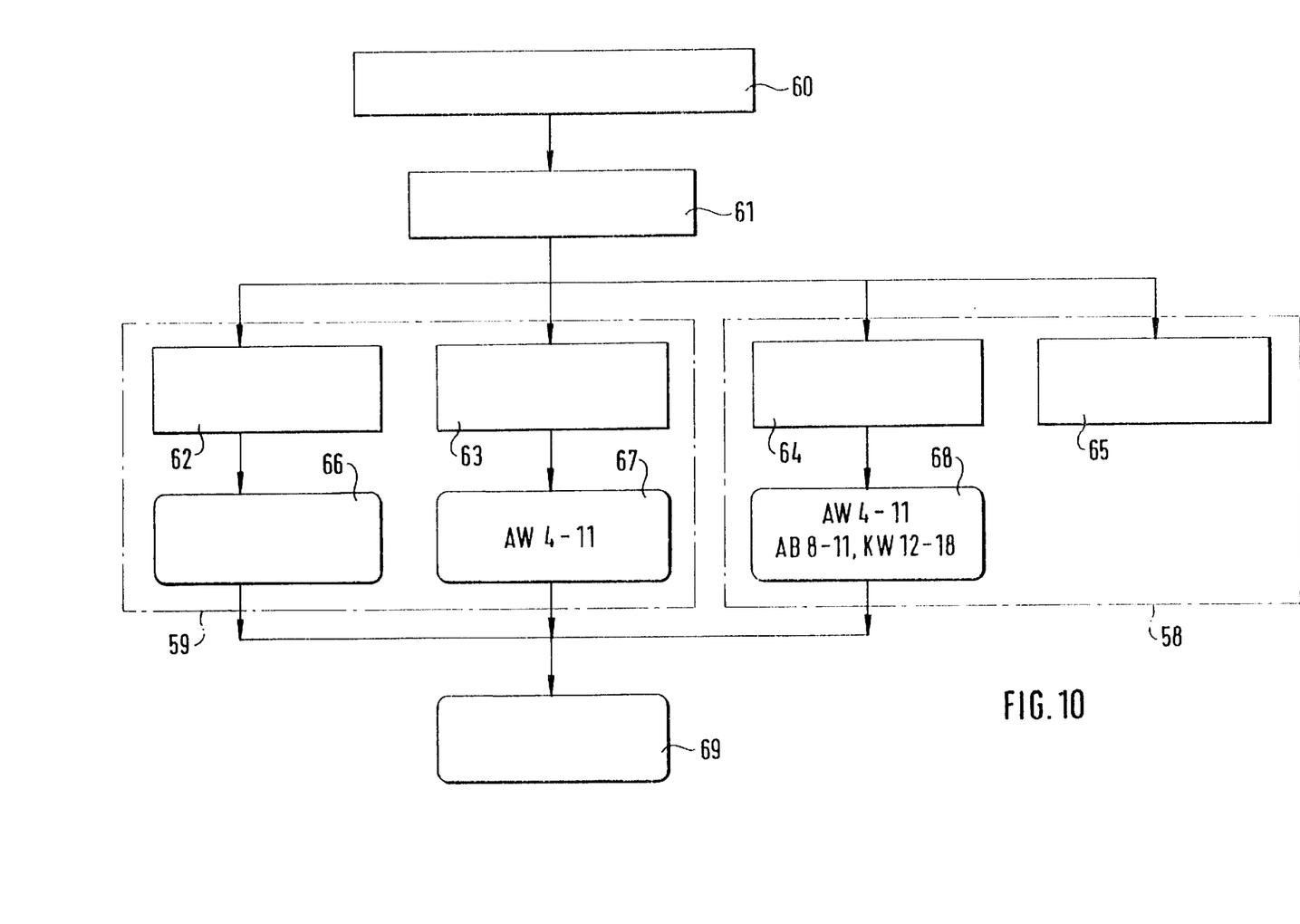
FIG. 10 shows a diagram of an arrangement for controlling control elements of different units of the calender and of the taking-off of the calender.

The means 58 and 59 are explained in further detail with the aid of FIG. 10, and serve the purpose of controlling shrinkage with the aid of different setting parameters in the take-off of the calender. Thus, for example, the means 58 influences the film temperature by increasing the coolant throughput through the calender rolls and blowing hot air onto the film edge zones or cold air onto the film middle. The means 59 reduces the constricting effect between the last calender roll and the first take-off roll through changing the take-off ratio, that is to say by changing the rotational speeds of the two rolls through using film edge guides or through blowing air onto the film take-off line.

An increase in the coolant throughput leads to a smoothing out of the temperature differences on the roll surface, and thus also to a smoothing out of the film temperature over the film width. Further temperature differences on the film surface, which can be caused by different thicknesses of the layer of air between the roll and the film, are corrected by blowing hot air onto the film edge zones or cold air onto the film middle. As a result, the glass transition temperature at the film edge and/or in the film middle is displaced via a change in relaxation time. The constricting effect between the last calender roll and the first take-off roll can be minimized via a reduction in the take-off friction or by the use of film holding mechanisms such as, for example, tenters. Blowing air onto the calender take-off line via an air knife smoothes out this take-off line, and thus reduces the constricting effect.

FIG. 10 shows a diagram of an arrangement of actuators for controlling the shrinkage on the basis of the measured values obtained by the shrinkage measuring instrument in the film middle and at the film edge. An actuator 60 feeds a control signal for shrinkage control into the actuator 61 in order to minimize the shrinkage difference ΔS. Controlling the shrinkage from the actuator 61 is not performed in an isolated fashion via individual further control elements for influencing an individual setting parameter. Rather, the various actuators 62 to 68 act on one another interdependently and simultaneously also influence quality properties of the film such as thickness tolerance, gloss, isotropy and the like. The actuators 62 and 66 control the friction between the last calender roll and the first take-off roll and regulate the speed of the last calender roll and the first take-off roll. The actuators 63 and 67 control the take-off speed of the calender, that is to say the rotational speeds of the take-off rolls 4 to 11 in accordance with FIG. 2. The actuators 62, 63, 66 and 67 form the means 59, represented in summarized form in FIG. 9, of the control loop.

The actuators 64 and 68 control the temperature of the take-off rolls 4 to 11 and of the chill rolls 12 to 18 in accordance with FIG. 2. An actuator 65 takes over the temperature control of the last calender roll 3 in FIG. 2. The actuators 64, 65 and 68 correspond to the means 58 of the control loop in accordance with FIG. 9. when controlling the shrinkage, it is preferred to regulate via the friction with simultaneous adaptation of the film thickness, but the remaining setting parameters such as the temperature control of the take-off and chill rolls as well as the temperature control of the last calender roll are controlled, like the rotational speed of the take-off rolls as well, individually, severally or all at the same time, in addition to the friction, if the friction control alone cannot effect the required regulation of the shrinkage. An actuator 69 undertakes the synchronous connection of the shrinkage control at the output side.

If it is not possible to change the shrinkage using the control possibilities described with the aid of the diagram described in FIG. 10, it is necessary for the speed control of the entire plant, that is to say the calender including the take-off, to be organized.

What is claimed is:

1. A method for continuously controlling the shrinkage of an amorphous film during removal from a calender having a plurality of sequential calender rolls followed by a plurality of sequential takeoff rolls and then optionally a plurality of chill rolls, comprising continuously measuring film shrinkage values in the middle and at an edge of the film over the film width and film length by measuring the dichroism or the birefringence of the film, calculating an average shrinkage for the middle and an edge of the film to form a shrinkage difference ΔS from a plurality of continuously measured shrinkage values, and wherein in the event of a deviation of greater than ±0.5% of the shrinkage difference from a prescribed shrinkage difference, altering at least one of the friction, temperature, or rotational speed parameters of at least one calender roll, take-off roll, or chill roll such that the shrinkage difference ΔS is kept within the range of the prescribed shrinkage difference ±0.5% deviation.

2. The method as claimed in claim 1, wherein the time up to reaching the glass transition temperature in the middle and at the edge of the film taken off from the calender, as well as the film widths on a last calender roll and a first take-off roll are measured, and wherein a shrinkage difference ΔS between the middle and the edge is determined in accordance with the formula $$\Delta s = \frac{t_{GM} - t_{GR}}{t_{GR}} + \frac{b_{LEW} - b_{EAW}}{b_{EAW}}$$
$$= t_{GM} / t_{GR} + b_{LEW} / b_{EAW} - 2$$

wherein $t_{GM}$ and $t_{GR}$ respectively are the times for reaching the glass transition temperature in the middle of the film and at the edge of the film and $b_{LKW}$ and $b_{EAW}$ respectively are the film widths on the last calender roll and the first take-off roll, and wherein the shrinkage difference ΔS is minimized.

3. The method as claimed in claim 2, wherein the temperature of the film surface is measured in the middle and at the edge on the take-off rolls by means of an infrared camera.

4. The method as claimed in claim 1, wherein the film width on a last calender roll and a first take-off roll is measured with the aid of a CCD device.

5. The method as claimed in claim 1, wherein for the purpose of shrinkage measurement, the film is transilluminated with linearly polarized laser light in the wavelength region from 400 to 900 nm, and wherein the orientation of the plane of polarization of the laser light is inclined with respect to the film longitudinal direction, as a result of which upon transilluminating the film the linearly polarized laser light is partially circularly polarized and reformed by optical means into a linearly polarized main beam which a downstream diffracting element splits into a positive integer number n component beams, each of which is directed onto a photoelement of a detector ring, equipped with a polarization filter.

6. The method as claimed in claim 5, wherein the direction of polarization of the polarization filter is rotated 360°/n in the radial direction of the detector ring about the optical axis of the main beam, and then measuring voltages generated by the photoelements to reproduce the intensity distribution of the light after transilluminating the film for conversion into a shrinkage value by means of a calibration curve for the measured film.

7. The method as claimed in claim 6, wherein n is in the range from 18 to 72.

8. The method as claimed in claim 6, wherein the calibration curve is calculated by a polynomial of 3rd degree having the formula $$f(y)=a+bx+cx^2+dx^3$$

wherein the anisotropy is f(y), the shrinkage is x, and the calibration curve parameters a, b, c, and d are characteristic of the film such that the shrinkage values correspond to the anisotropy values in the case of a measurement without film in the beam path.

9. The method as claimed in claim 1, wherein the film temperature is controlled over the film width by increased coolant throughput in the chill rolls.

10. The method as claimed in claim 1, wherein hot air is blown onto a film edge zone in order to alter the film temperature over the film width.

11. The method as claimed in claim 1, wherein cold air is applied to the film middle in order to alter the film temperature over the film width.

12. The method as claimed in claim 1, wherein film shrinkage between the last calender roll and the first take-off roll is minimized by altering the rotational speeds of the take-off rolls.

13. The method as claimed in claim 1, wherein the film is guided at the edges by means of tenters.

14. The method as claimed in claim 1, wherein film shrinkage is reduced by applying compressed air from an air knife to the last calender roll.

15. The method as claimed in claim 1, comprising at least one step selected from the group consisting of:
(a) controlling the film temperature over the film width by increased cooling throughput in the chill rolls;
(b) altering the film temperature over the film width by blowing hot air onto a film edge;
(c) altering the film temperature over the film width by applying cold air to the film middle;
(d) altering the speeds of the takeoff roll to thereby minimize film shrinkage between the last calender roll and the first take-off roll;
(e) guiding the film edges by means of tenters; and
(f) applying compressed air from an air knife to the last calender roll to thereby reduce film shrinkage.

16. An arrangement for continuously controlling the shrinkage of an amorphous film during removal from a calender having a plurality of sequential calender rolls followed by a plurality of sequential take off rolls and then optionally a plurality of chill rolls, comprising a shrinkage measuring instrument which supplies measured data concerning the shrinkage of the film to a connected measured-data computer which is connected via an interface to a master computer and to a screen display, wherein characteristic calibration curve parameters of different film types and shrinkage deviations and/or shrinkage limits are stored in the master computer and are fed into the measured-data computer which uses a calculated shrinkage difference and a measured shrinkage difference between the film middle and a film edge to determine a deviation in the shrinkage difference ΔS and to relay it to the master computer, and wherein the master computer is connected to actuators capable of altering the friction, temperature, and the rotational speed of the calender rolls, the take-off rolls, and chill rolls, and means for independently applying control to the actuators.

17. The arrangement as claimed in claim 16, wherein the shrinkage measuring instrument has a frame having a U-profile, and a measuring head comprising a light source and a receiver which can be displaced along limbs of the U-profile, the lengths of the limbs being selected such that the measuring head can be displaced into the middle of a film which runs between the two limbs as well as between the light source and the receiver.

18. The arrangement as claimed in claim 17, wherein two linear guides are arranged near the calender transverse to the running direction of the film and are fitted with two guide carriages on which the shrinkage measuring instrument is fastened, and wherein the guide carriages are driven by a motor.

19. The arrangement as claimed in claim 17, wherein the light source is a laser with a power of 2 to 4 mW in the red wavelength region, and wherein the receiver comprises a single photoelement.

20. The arrangement as claimed in claim 17, wherein the light source and the receiver are each individually installed in cylindrical tubes, wherein the cylindrical tubes are mounted opposite one another perpendicular to the limbs of the U-profile and are adjusted about the optical axis of the light-source receiver, and wherein a rotary part with a polarization filter is mounted on an end face of each cylindrical tube pointing towards the film.

21. The arrangement as claimed in claim 20, wherein each cylindrical tube is connected on the outside to a toothed disk over which there is guided an endless flat toothed belt which runs around a further toothed disk of a shaft which is driven by a motor.

22. The arrangement as claimed in claim 21, wherein seated on the shaft are the two toothed disks around which the endless flat toothed belt each runs, wherein a synchronous rotation of the light source and receiver is produced by the rotation of the shaft, and wherein the direction of rotation of the shaft and/or the motor is reversible.

23. The arrangement as claimed in claim 20, wherein the cylindrical tubes are mounted in pedestal bearing housings.

24. The arrangement as claimed in claim 20, wherein the positions of the polarization filters with respect to the light source and the receiver can be adjusted in the rotary parts.

25. The arrangement as claimed in claim 16, wherein a measuring head of the shrinkage measuring instrument comprises a laser as the light source and a receiver which comprises optical means, a diffracting element, and a detector ring with a positive integer number n of photoelements, wherein each photoelement is equipped with a polarization filter, and wherein the measuring head is arranged in a U-profile which traverses the machine direction.

26. The arrangement as claimed in claim 25, wherein the number n of the photoelements is in the range from about 18 to about 72.

27. The arrangement as claimed in claim 25, wherein the direction of polarization of the polarization filter is rotated in each case by 360°/n in the radial direction of the detector ring about the optical axis of the main beam of the light source.

28. The arrangement as claimed in claim 25, wherein optical means are positioned between the receiver and the detector ring which reforms circularly polarized light transmitted through the film into a linearly polarized main beam which is split by a downstream diffracting element into a positive integer number n component beams, each one of which impinges on a polarization filter and a photoelement situated therebehind.

* * * * *